(12) United States Patent
Le Pivert

(10) Patent No.: US 9,399,101 B1
(45) Date of Patent: Jul. 26, 2016

(54) NEEDLE SYSTEM FOR TISSUE PERFUSION

(71) Applicant: Patrick Jean Le Pivert, Jupiter, FL (US)

(72) Inventor: Patrick Jean Le Pivert, Jupiter, FL (US)

(*) Notice: Subject to any disclaimer, the term of this patent is extended or adjusted under 35 U.S.C. 154(b) by 712 days.

(21) Appl. No.: 13/758,996

(22) Filed: Feb. 4, 2013

Related U.S. Application Data

(60) Provisional application No. 61/632,992, filed on Feb. 3, 2012.

(51) Int. Cl.
*A61M 5/32* (2006.01)
*A61F 7/12* (2006.01)
*A61B 18/02* (2006.01)

(52) U.S. Cl.
CPC ............. *A61M 5/329* (2013.01); *A61B 18/02* (2013.01)

(58) Field of Classification Search
CPC .............. A61B 18/02; A61M 2018/00041; A61M 2018/0212; A61M 2018/00005; A61M 2018/00577; A61M 2018/1861; A61M 2018/1869; A61M 2018/00101; A61M 2025/0681
See application file for complete search history.

(56) References Cited

U.S. PATENT DOCUMENTS

| | | | |
|---|---|---|---|
| 7,628,780 B2 | 12/2009 | Bonner et al. | |
| 7,833,187 B2 | 11/2010 | Le Pivert et al. | |
| 8,088,413 B2 | 1/2012 | Le Pivert et al. | |
| 8,380,299 B2 | 2/2013 | Le Pivert | |
| 8,382,698 B2 | 2/2013 | Le Pivert et al. | |
| 2010/0274178 A1* | 10/2010 | LePivert | A61B 18/02 604/21 |

* cited by examiner

*Primary Examiner* — Rebecca E Eisenberg

(57) ABSTRACT

A perfusion needle system for the direct simultaneous injection of a therapeutic substance fluid within a target tissue during cryothermal ablation of the tissue includes at least one cryogenic probe for insertion in the tissue, the probe having a cooling tip for selective cooling and thawing of the tissue. An injection syringe contains a fluid substance and an injection needle is fluidly communicative with the injection syringe. The injection needle includes a port at a proximal end of the needle for connecting to the injection syringe and a tubular needle body having a wall forming said tubular body, which includes an internal insulative layer, which defines a central lumen extending through the body. An injection tip devoid of the insulative layer is affixed to a distal end of the injection needle and defines at least one opening through a side the tip and is fluidly communicative with the lumen.

17 Claims, 9 Drawing Sheets

NEEDLE SYSTEM FOR TISSUE PERFUSION

CROSS-REFERENCE TO RELATED APPLICATION

This Non-Provisional Utility application claims the benefit of U.S. Provisional Patent Application Ser. No. 61/632,992, filed on Feb. 3, 2012, which is incorporated herein in its entirety. Applicant respectfully notes Feb. 3, 2013 falls on a Sunday. Therefore, Applicant is afforded until the next business day to timely submit a copending Non-Provisional Application.

FIELD OF THE INVENTION

The present disclosure generally relates to apparatuses and methods for perfusing tissue with therapeutic liquid medicaments. More particularly, the present disclosure relates to a sheathed perfusion needle system for perfusing a tissue with a therapeutic fluid substance during simultaneous treatment of that tissue with one or more separate energy delivering devices in close proximity thereto.

BACKGROUND OF THE INVENTION

Cancerous tumors are the subject of numerous treatment methodologies depending on the types and locations of the tumors. The primary methodologies involve surgical excision of the tumor, radiology, or chemotherapy typically delivered intravenously to a patient. One result of intravenous (IV) chemotherapy is that the chemotherapy substance is delivered throughout the patient's entire body with significant and deleterious side effects being suffered by the patient. Ideally, cancerous tissues are desired to be treated locally, or in situ, to the individual tumors thereby minimizing the exposure of the patients body to any adverse effects of the treatment.

In situ tumor destruction with cryogenics, radiofrequency or laser ablation has received increasing attention as a treatment modality for focal cancer such as liver, lung, pancreas, prostate, breast, node, and kidney. However, a number of recurrences at sites of ablation are seen from 10% to 40% for cryogenic treatment. Additionally an increased use of combined therapies with these ablative methods, such as chemotherapy, radiotherapy and immunotherapy, are aiming at optimizing their safety and local efficacy. They can also potentially increase the overall survival, and the host defense against micro-metastatic disease, or distant metastases.

A number of therapeutic substances such as drugs, chemical, protein, biologic or cell, and injection techniques are in use along with various strategies to combine their administration with that of the focal ablative technique. For instance, cryoablation (i.e. the in situ destruction of tissue by deep freezing with cryogenic applicators such as cryoprobes or cryoneedles) has been combined with systemic (IV) or regional, Intra Arterial (IA), chemotherapeutics or local chemical (such as ethanol, EtOH) injection to improve local ablative results, particularly for large tumors or tumors located in the vicinity of risky structures as disclosed in U.S. Pat. No. 7,344,530 to Bischof. Some of the therapeutic substances are mixtures of drugs in solution, suspension or emulsion that may include drug carriers, vectors, radiocontrast agents or dye that serve as markers or tracers for assessing drug distribution and clearance during image-guided interventions.

A great number of thermal or cryothermal devices exist already that are able to deliver energy to target tissue within small instruments so that they can be used for various minimally invasive (MIS) approaches (percutaneous, endoscopic, endovascular catheter) or through natural orifices and open surgery. In a purely scientific sense, energy delivery means the addition of energy resulting in an increase in the thermal profile of the tissue. As used herein, energy delivery is defined as meaning energy transfer to or from the subject tissue resulting in an elevation of tissue temperature (addition of energy) or a cooling of the tissue temperature (removal of energy).

An even greater number of perfusion devices for perfusing, infusing or injecting drugs or substances within the patient's body or within target tissue exist already. They are needle-like (rigid, semi-rigid or formable shaft) or catheter-like (flexible shaft). A preferred method for perfusing a tumor with a drug is to directly inject the therapeutic substance within the interstitial compartment of the tumor to maximize its effectiveness and minimize its systemic side effects. These methods, such as chemoablation, intra tumor (IT), or intralesional (IL) therapy, are growing in use since they have many advantages such as: Narrow therapeutic index drugs can be safely injected and at a much higher concentration than when systemically injected. Also, drugs can be injected in brain tumors that could not otherwise penetrate the blood brain barrier. These techniques are minimally invasive, less aggressive, and less costly than open surgery, to cite only a few.

Various methods for combining the focal energy delivery with the administration of therapeutic fluids, drugs or substances have been designed. These methods generally administer the drug before or after the delivery of energy (U.S. Pat. No. 7,083,612 B2 to Littrup), either systemically, regionally or locally (interstitially). U.S. Publication 2008/0027419A1 to Hamel et al. shows a delivery device for a treatment agent that combines a cryoprobe and a sealed delivery device provided with a puncture member to break the seal. Such a device does not allow for any control of the substance flow based on the change of physical state of the substance—i.e. liquid to solid and vice versa—and prevention of reflux during injection within tissue based on the physical change of state of the tissue water and structure. In addition, there is no provision for sensing a critical parameter such as fluid pressure before, during, and after substance delivery that allows for fine control of fluid substance delivery. There is no provision for a system that would timely control the cooling and delivery sequences necessary for successfully injecting the substance into tissue.

Although the interstitial injection of drugs and substances has shown some potential advantages, it has not been yet fully exploited. For instance, fluids are injected around the region of energy delivery to protect sensitive structures from unwanted harmful effect. For example, saline can be injected during cryogenic-mediated breast tumor ablation to protect the skin from freezing. Other examples of fluid injection include the sensitization of the tissue to thermal ablation, and for instances with injection of saline for increasing the area of thermal ablation during energy deposition with a radio frequency (RF) device, or with sensitizing drugs as disclosed in U.S. Pat. No. 7,344,530 to Bischof. Multiple Studies demonstrate that the interstitial distribution and retention, i.e. residence time of a drug substance injected systemically (IV) or regionally (IA) would be improved with the simultaneous administration of the drug and the energy, along with a potential for better safety and effectiveness. Additionally, such combinations could also activate the host immune response against local and disseminated cancer cells. For instances during cryosurgery and simultaneous local injection of a drug in a fluid form in the vicinity of the frozen tissue the forces exerted on the fluid flow and the resulting tissue structural changes pave the way for driving or transporting substances within an interstitial matrix, for increasing cell membrane permeation to the substance, and for modifying the extracellular matrix porosity (i.e. the pore structure) resulting in an improved substance retention or residence time like into the mesh of a net. Some of these thermo-mechanical changes result in prevention of backflow of the substance along the needle track, along with convective flow of the substance ahead of the ice front during cryosurgery. However, due to the shortcomings of existing perfusion needles, such as incapability of maintaining the substance in a liquid state or at their temperature range of structural integrity during the administration of heat energy or the deprivation of heat energy (cooling), there is an inability to perform the interstitial injections during and in the close vicinity of the energy delivery devices. For instance, most cytotoxic drugs can be combined with cryoablation but their flow will stop when the temperature of the injection needle wall drops to their freezing point, i.e. about 0° C., and they will be denaturated by thermal shock (sudden drop of temperature followed by temperature rise), particularly if they are made of proteins or cells, when in contact with a cooling source such as a cryoneedle or cryoprobe.

Therefore there is a need for a tissue perfusion needle that can maintain the flowability and structural integrity of a substance during its transfer through the needle lumen until it is interstitially delivered to the target tissue concurrently submitted to focal cryoablation.

During an operative procedure the perfusion needle is guided (utilizing direct vision or other imaging methods such as CT, MR, US, etc.) to a location that is thought as best for optimal drug distribution and drug permeation over the target tissue. However, there is no assurance that the elected site of drug delivery is best for optimal delivery. It is known that a fibrous tissue is more difficult to permeate than a soft tissue and that a low interstitial pressure is better than a high pressure for the drug bulk flow. Consequently, it would be useful to know beforehand whether the site of injection is at relatively high or low pressure. The relative pressure being a parameter that would help initiating perfusion at injection or infusion pressure that would be slightly grander.

Therefore, there is a need for a sensing method for the perfusion procedure that would detect the perfusion needle patency, the proper needle priming, absence of air, change of substance physical state and the tissue target pressure at all times before, during and after a procedure.

There is an unmet need for a needle to deliver the substance at a time and location when the tissue is under cryoablative therapy, partially or wholly frozen and when an unfrozen part of such tissue should be permeated with the fluid substance.

There is also an unmet need for such a needle to sense the moment when in the course of the cryoablative process the substance is still in a liquid and injectable state, even though the needle is immersed within the frozen tissue.

There is also a need for a combined cryoablative and substance injection method that is based on the target calculated volume, target location, target shape or characteristics. A method that specifies the location, number, characteristics of the injection needle and needle tip (deployable, multi-hole and side hole tip, tip bevel, echogenicity), the injection sites, rate and the substance characteristics or temperature, so that the liquid substance flow, distribution and retention are optimized, to insure a homogeneous and complete permeation of the target with the diagnostic/therapeutic substance.

SUMMARY OF THE INVENTION

The present disclosure is generally directed to a perfusion needle system for the direct simultaneous injection of a therapeutic substance fluid within a target tissue during cryothermal ablation of the tissue includes at least one cryogenic probe for insertion in the tissue, the probe having a cooling tip for selective cooling and thawing of the tissue. An injection syringe contains a fluid substance and is fluidly connected to a pressure line. The pressure line is configured to interface with a pressure sensing system for determining pressure of the fluid therapeutic substance in the pressure line. An injection needle is fluidly communicative with the pressure line. The injection needle includes a port at a proximal end of the needle for connecting to the injection syringe and a tubular needle body having a wall forming said tubular body, which includes an internal insulative layer, which defines a central lumen extending through the body. An injection tip devoid of the insulative layer is affixed to a distal end of the injection needle and defines at least one opening through a side the tip and is fluidly communicative with the lumen.

In a second aspect, the injection needle tip has a smaller diameter than the needle body.

In another aspect, the injection tip defines a single opening at an end of the injection tip.

In yet another aspect, the injection tip defines a plurality of side openings substantially equally spaced about a periphery of the injection needle tip and longitudinally equidistant from an end of said injection tip.

In a further aspect, the fluid therapeutic substance is selected from a group consisting of a chemotherapeutic, a cytotoxic, a cytostatic, a chemical solvents, a biologic drug, a vaccine, a gene, a vector, a radioisotope, a radioseed, a radiosensitizer, a protein, a cryoprotective solution, and a cryosensitizing solution.

In a still further aspect, the pressure sensor is positioned the injection needle proximate to the injection tip, the pressure sensor being electrically communicative with a pressure monitor for displaying a sensed pressure in the patient tissue at the injection tip.

In another aspect, the injection needle includes a central tube extending within the lumen, the central tube having a diameter smaller than the lumen and, in combination with the lumen, defines a gap between the central tube and the lumen, the gap fluidly communicative with the syringe.

In another aspect the central tube is a cryogenic cooling tube wherein the cryogenic cooling tube is selectively operable to cool tissue and fast rewarm tissue.

In a still further aspect the tubular needle wall and the insulative layer are homogenous and are fabricated from a single material.

In yet another aspect, a perfusion injection needle comprises a port at a proximal end for connecting to an injection syringe and a tubular needle body having a wall forming the tubular body. An insulative layer is affixed to an interior of the wall, the insulative layer defining a central lumen extending through the body. An injection tip is affixed to a distal end of the injection needle and is devoid of the insulative layer. The tip defines at least one opening extending through a side thereof and fluidly communicative with the lumen.

In another aspect the injection needle tip has a smaller diameter than the needle body.

In still another aspect the injection tip defines a plurality of side openings substantially equally spaced about a periphery of the injection needle tip.

In yet another aspect the needle further includes a pressure sensor proximate to the injection tip. The pressure sensor is connected to an electrically communicative cable for connection with a pressure monitor for displaying a pressure sensed at the injection tip.

In another aspect the needle further includes a central tube extending within the lumen. The central tube has a diameter smaller than the lumen and in combination with the lumen, defines a gap between the central tube and the lumen and forms a passageway therealong.

In still another aspect the central tube is a cryogenic cooling tube wherein the cryogenic cooling tube is selectively operable to cool tissue and fast rewarm tissue.

In yet another aspect the tubular needle wall and the insulative layer are homogenous and are fabricated from a single material.

In a still further aspect, a method for controllably injecting a therapeutic substance to a tissue simultaneously subjected to a cryoablation treatment includes the steps of using a perfusion needle system of the type comprising at least one cryogenic probe having a cooling tip, an injection syringe containing a fluid therapeutic substance and connected to a pressure line including a pressure sensor and at least one injection needle fluidly communicative with the pressure line wherein the injection needle further includes a port at a proximal end for connecting to the injection syringe, a tubular needle body having a wall forming the tubular body, an insulative layer affixed to an interior of the tubular wall and defining a central lumen extending through the body, and an injection tip affixed to a distal end of the injection needle, the tip being devoid of the insulative layer and defining at least one opening extending through a side of the injection tip and fluidly communicative with the lumen. The tip of the injection needle is positioned within a target tissue to be treated in a patient, and the cryogenic probe is positioned proximate to the target tissue to be treated such that the injection needle will be within a zone of the tissue to be frozen by the cryogenic probe. A base line fluid pressure is measured and the cryogenic probe is activated to produce a zone of frozen tissue extending about the body of the injection needle excluding the tissue about the injection needle tip. The fluid therapeutic substance is delivered through the injection needle tip when the zone of frozen tissue approaches the injection needle tip, and a desired dose of the fluid therapeutic substance is allowed to distribute through the target tissue at a pressure above the baseline pressure and propagated away from the zone of frozen tissue. The pattern and volume of substance distribution within the target tissue is assessed. The injection needle is removed from the target tissue when the pressure reading is at or below the baseline pressure, and the cryogenic probe is removed when the frozen zone of the target tissue has thawed.

In another aspect, the targeted tissue is a tumor and the tissue frozen zone encompasses the entire tumor.

In a further aspect, the fluid therapeutic substance is at least partially distributed in tissue outside the margin of the tumor.

In a still further aspect, a plurality of injection needles and a plurality of cryoprobes are inserted in the target tissue, each cryoprobe producing a frozen zone and further wherein the frozen zones of adjacent cryoprobes overlap one with the other and each injection needle delivers a dose of fluid therapeutic substance overlapping with a dose of fluid therapeutic substance of an adjacent injection needle.

These and other features, aspects, and advantages of the invention will be further understood and appreciated by those skilled in the art by reference to the following written specification, claims and appended drawings.

BRIEF DESCRIPTION OF THE DRAWINGS

The invention will now be described, by way of example, with reference to the accompanying drawings, where like numerals denote like elements and in which.

Like reference numerals refer to like parts throughout the various views of the drawings.

DETAILED DESCRIPTION OF THE INVENTION

Figure 1:
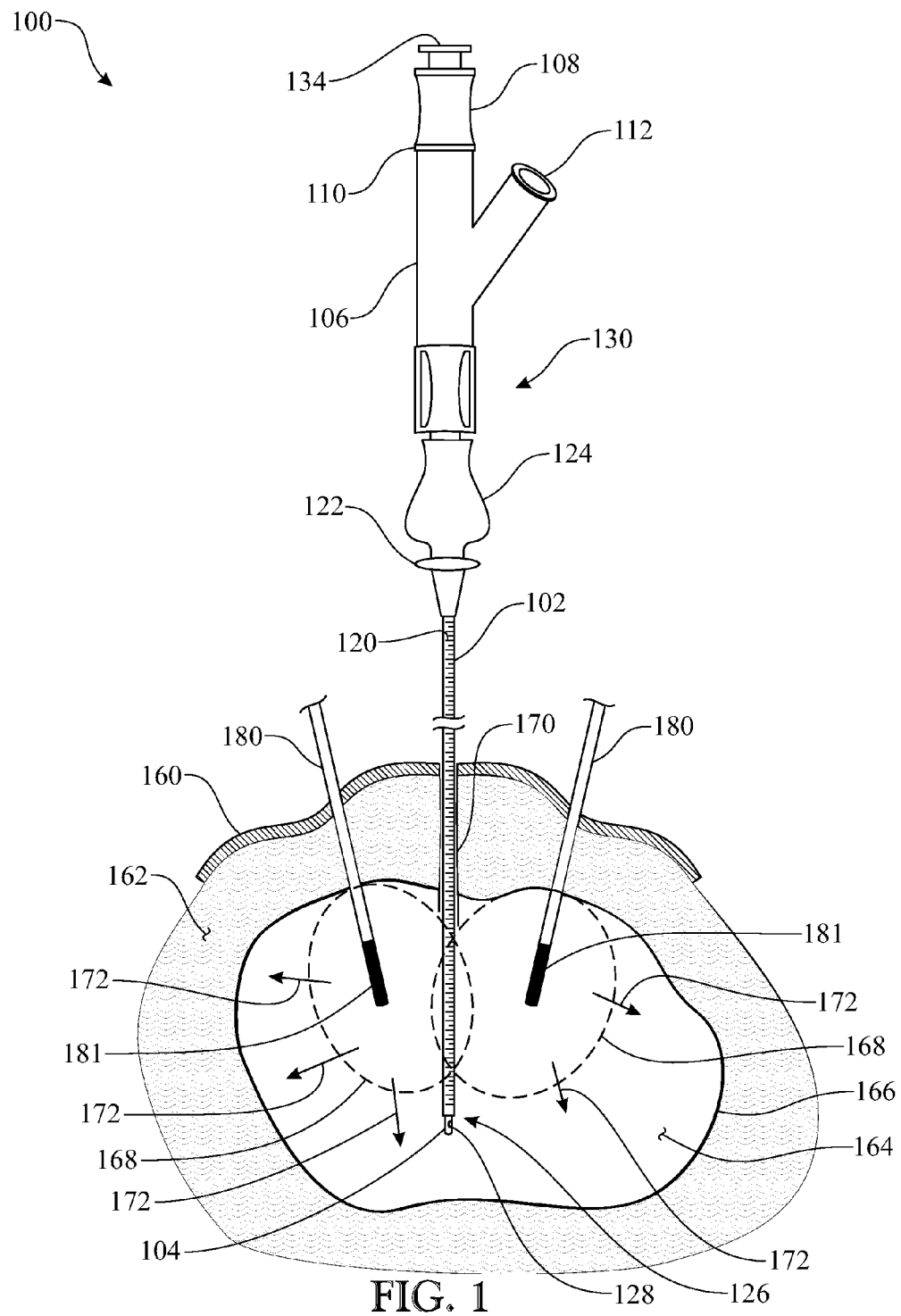
FIG. 1 presents an isometric view of an injection needle system for treating tumors and embodying the present invention, wherein an injection needle is located in the vicinity of two activated cryoprobes within the tumor.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

DEFINITIONS

Certain definitions are deemed to be necessary to provide explanation and knowledge of designated terms for the understanding of the embodiments described herein.

Perfusion: The injection and/or infusion of substance within any zone, frozen and/or unfrozen of the cryotreated tissue, during the cooling and/or warming period of a cryoablative procedure, and/or just before or after cryoablation intra-operatively.

Cryoprobe or cryoneedle: A cryoablative instrument used to cool and freeze target tissue by any known modality.

Substance: Any diagnostic, therapeutic drug, or mixture that is or can be injected in liquid suspension, solution or emulsion within the body of a human or animal patient. Drugs can be free or formulated (particulate, nanocarriers, microcapsule, matrix-based, etc.). Drugs can be non-specific or specific to target structures or molecular receptors. A substance can also be any diagnostic, therapeutic substance, or mixture of interest that is capable of flowing in liquid state and is injected through the inlet port of the needle perfusion lumen for release at the distal end openings of a delivery structure. Substances can be drugs, either free or bound to carriers, chemotherapeutics, chemicals, hormones, small molecules, peptides, proteins, polynucleotides, biological molecules, viruses, cells (e.g., stem cells, skeletal myoblasts, etc.), cell membrane receptors, eutectic compositions as in U.S. Publication 2006/0122588 A1 to Bischof, viscous composition as in U.S. Publication 2009/0208422 A1 to Mardor, or additives as in U.S. Pat. No. 5,654,279 to Rubinski. A substance can be used alone or combined. Of particular interest for use with the present invention are water miscible organic solvents as described in U.S. Pat. No. 6,753,005 B1 to Pietronigo. For instance, a chemotherapeutic can be associated with a solvent, or a sclerosant substance. Substances experience a change of state and physical properties when they are flowing along a cryogenic source during a procedure. They have compatible thermal and chemical properties with the needle material. One advantage of the present invention is its ability to change the viscosity of the injected substance without any need to re-formulate the substance beforehand.

Patient: A patient may be of any species, human, domesticated animal, dog, cat, bird, pet, fish, hamster, rat, gerbil, etc. In preferred embodiments, the patient is a human. The patient may be suffering from a disease such as benign or malignant solid tumor, cardiac disease, diabetes, Parkinson's disease, genetic defect, etc.

Solid Tissue: Solid tissue refers to any tissue or organ within a patient's body. The methods described herein may be used to deliver any agent including cells into the solid tissue. The solid tissue may be a normal organ (e.g., heart, pancreas, brain, liver, kidney, skeletal muscle, etc.) or an abnormal growth such as a benign or malignant tumor (solid tumor or tumor). In preferred embodiments, the solid tissue will provide resistance to the introduction of additional matter such as a liquid or cells. In preferred embodiments, the solid tissue is a solid tumor in the brain, liver, breast, prostate, pancreas, lung, etc.

Substance Perfusion Volume, Distribution Volume and Pattern: The term "substance perfusion volume" (Vi) refers to the amount of an agent needed to elicit a desired biological response. In a preferred embodiment, the effective perfusion volume of an agent is delivered using a minimum number of injections or needle passes so as to not damage the tissue surrounding a target organ by using multiple injections. Therefore, each injection should preferably result in an "optimal" distribution pattern (Vd), concentration and retention of a substantial portion of the agent being delivered within the target organ. For example, in the case of a cancerous tumor, the effective perfusion volume of chemotherapeutics is the volume necessary to kill all the cancer cells of the selected tumor. In the case of tissue damage or degeneration, the effective perfusion amount of cells is the amount necessary to improve the function or structure of the abnormal or damaged tissue. The ratio Vd/Vi is one of many parameters used to determine the efficacy of the perfusion device for distributing the perfused substance to the target volume.

Perfusion distance: The distance measured between the icing zone of the tissue and the perfusion needle outlet(s).

Perfusion lumen clearance: The lumen area or volume defined by the distance measured from the outer wall of the cryoneedle cooling source and shaft to the inner wall of the perfusion tubing about the cryoneedle. Such clearance may vary with the connection to a cryoneedle of various gauge perfusion sheaths, or with the use of various cryoneedle gauges for a set perfusion needle gauge.

Frozen Zone, Ice Ball, or Ice Zone: The tissue that is cooled to a temperature below the tissue freezing temperature. The remainder of tissue cooled to a temperature below body temperature but not frozen is the hypothermal region.

Interstitial, Intralesional (IL), or Intratumoral (IT): The site of perfusion (i.e. injection or infusion) for a substance that is deposited within the extracellular matrix (ECM) of the target tissue, excluding the intravascular compartment. A single site or multiple sites may be injected simultaneously or sequentially.

A substance in liquid state is either a solution, an emulsion or a suspension that contains one or many diagnostic or therapeutic agents, as in a mixture, and must keep its integrity and activity upon its release into a target tissue. When a target tissue is experiencing abrupt or sudden localized thermal changes about a heat source such as a cryoprobe, an injection needle located in the vicinity of the heat source will bear simultaneous thermal changes as well as the liquid substance(s) contained in its injection lumen. Subsequently, the substance may lose its ability to flow or may undergo structural physico-chemical changes that decrease or inhibit its effectiveness. The embodiments of a needle described herein allow interstitial thermal/cryothermal therapy and simultaneous integral substance injection.

DESCRIPTION OF EMBODIMENTS

In one exemplary implementation of the invention, an injection needle system 100 is shown in FIG. 1 treating a patient. The patient being treated has a tumor 164 within the patient's healthy bodily tissue 162 wherein the tumor 164 is defined by tumor margin 166 describing the outer limits of the tumor 164 to be treated. Two activated cryoprobes 180 have been inserted through the patient's skin 160 and healthy tissue 162 into the mass of the tumor 164. Each of the cryoprobes 180 has a cooling tip 181 which, when activated, produces a cooling sequence that aims to freeze the site of the tumor 164 at a temperature that kills the cancer cells therein. Each cooling tip 181 creates an outwardly growing ice front 168 (isotherm at 0° C.). Each ice front 168 develops substantially symmetrically as an ovoid about the respective cooling tip 181.

The injection needle system 100 aids in the treatment of the tumor 164 and includes an injection needle 102 having a depth stop 122 at a proximal part 130 of the needle system 100 and an injection tip 104 at a distal end 126 of the needle 102. The injection needle 102 includes a plurality of regularly spaced depth markings 120 along a length thereof to aid in determining the depth to which the injection needle is inserted within the patient's body. The injection tip 104 defines at least one and preferably a plurality of openings 128 substantially equally spaced therearound and fluidly communicative with an internal lumen 118 (FIG. 2) of the injection needle 102. The depth stop 122 of the injection needle 102 is affixed to a hub 124 (usually a Luer lock female). The depth stop 122 will be moved to contact the surface of skin 160 during a procedure when the needle 102 is positioned within the tumor 164. The hub 124 is coupled, either permanently or removably, with connector 106. Connector 106 is provided with a first Luer port 110 and a second Luer port 112. Injection needle hub 108 connects tightly—Luer lock-, to the first Luer port 110 as well as to an inner injection tubing body (not shown) and to injection tip 104 at distal zone 126. A substance injection syringe 134 or injection line (not shown) can be connected to injection needle hub 108 and an injection/aspiration source (syringe with plunger lock, pump) can be connected to second Luer port 112.

Figure 2:
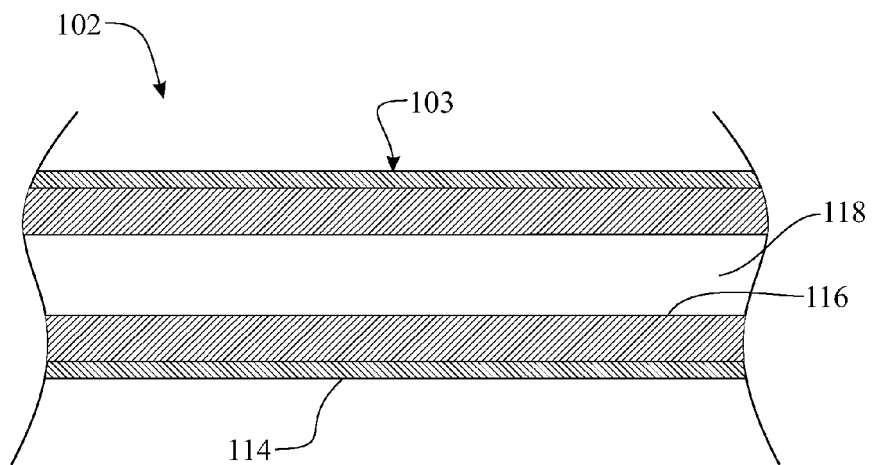
FIG. 2 presents a cross-sectional view of the body of an injection needle.

A first embodiment injection needle 102 is illustrated in cross-section in FIG. 2, wherein insulated injection needle 102 has a sheathed, insulated tubular body 103. The insulated needle body 103 includes a needle wall 114 forming the tubular body 103, an insulation layer 116 affixed to an interior of the needle wall 114, and an injection lumen 118 for transmitting the substance therethrough. The needle wall 114 is preferably fabricated of stainless steel for any other metal, alloy, or composite known within the art). The insulation layer 116 comprises a material that has low thermal conductivity including, but not limited to, foams of polyurethane, silicone, polyvinyl alcohol or other thermoplastics. Typically, the diameter of the needle 102 is small, from 22 gauge to 19 gauge to allow for minimal invasiveness during a percutaneous procedure. Such minimal invasiveness is crucial since the thinner the diameter of the needle the lower the risk of reflux of substance through needle track 170 (FIG. 1). The insulation layer 116 coats the interior of needle wall 114 and defines the lumen 118 for the passage of the treatment substance therethrough. The injection lumen 118 is quite small and can range from 27 gauge to 23 gauge. The thermally insulated sheathed needle body 103 permits injecting a fluid substance that would otherwise freeze if immersed into a tissue that is undergoing cooling and cryosurgical freezing. The insulated sheathing of the body 103 functions in like manner during a heating cycle wherein the substance would heat up and possibly degrade or melt if the needle 102 were plunged into a tissue submitted to thermal ablation. The delivery tip 104 of the sheathed needle 102 is non-insulated thereby permitting cooling of the medium or target tissue in contact with the tip 104 is measured with the pressure changes of the substance transmitted through the lumen 118 thereby providing an indication that the injection should be initiated at that time before freezing and/or after melting and possibly blocking flow of the substance within the lumen 118.

During a cryosurgical procedure to treat tumor 164 as illustrated in FIG. 1, one or multiple cryoprobes 180 are inserted within the tumor 164. The injection needle 102 is positioned in the vicinity of the two activated cryoprobes 180 also within the tumor 164. The ice front 168 (isotherm 0° C.) that grows outwardly off the cooling tips 181 of both cryoprobes 180 is shown overlapping the injection needle body 102. A therapeutic solution as the treatment substance having a freezing point at 0° C. is injected within the tumor 164 utilizing injection needle system 100. Since the cryoprobes are touching or close to the injection needle 102, the insulation layer 116 protects the therapeutic solution from cooling or freezing as a result of the heat transfer induced by the tissue cooling. Therefore, the therapeutic solution is not frozen and can be injected in the vicinity of the cryoprobes 180, provided that the delivery tip 104 is located within an unfrozen region (outside the ice front 168 that the pressure readings can assess).

Figure 3:
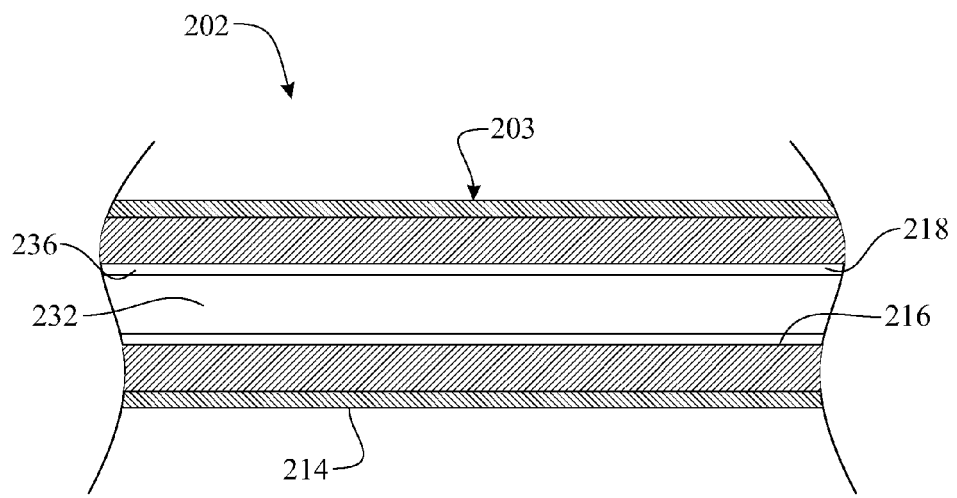
FIG. 3 presents a cross-sectional view of the body of the injection needle shown in FIG. 2 and further including a cooling tube in the central lumen.

An alternative embodiment injection needle 202 for use in injection needle system 100 is illustrated in FIG. 3 in cross section, wherein the injection needle 202 has an insulated body 203 having a needle wall 214 and an insulation layer 216 defining a lumen 218. The lumen 218 is of a larger diameter and designed to accommodate a small cryogenic cooling tube 232 the size of which can range from 25 gauge to 21 gauge, or larger cryogenic tubing from 21 gauge to 17 gauge. The cooling tube 232 is smaller than the lumen 218 defined by the insulation layer 216 and a passageway 236 is located between the cooling tube 232 and the insulation layer 216 defining the lumen 218. The insulation layer 216 can also be made of material of low thermal conductivity such as PTFE, ETFE FEP, FPA, Teflon, urethane, silicone, polyethylene, etc.

Referring again to FIG. 1, during a procedure utilizing injection needle system 100 incorporating injection needle 202, aspirating through second Luer port 112 creates a vacuum within needle 202, the insulation layer 216 prevents inner injection tubing body 232 from experiencing the thermal changes of the needle body 202. The injection syringe 134 connected to hub 108 provides the force for moving the substance through the injection tubing body 232. The injection tip of injection needle 202, similar to injection tip 104 of injection needle 102, is located distal to injection tubing 232 and carries the substance through openings 128 to target extracellular medium (ECM) contained within tumor margin 166 within the patient's body. The needle tip 104 defines a plurality of side openings 128 about a periphery of the tip 104 and equidistant from the end of injection tip 104 to permit optimizing the distribution pattern of fluids transmitted from lumen 118 into the targeted tissue. The needle body 103 and the cryoprobes 180 have been inserted percutaneously through skin 160 into the target tumor 164. Arrows 172 shown diverging from the ice front 168 indicate the direction of ice propagation during continuous cooling. The non-thermally insulated needle tip 104 is located distal to ice front 168 (isotherm 0° C.), which permits injecting the substance through opening 128. During an alternate procedure utilizing the injection needle system 100, injecting a low heat conductivity substance through second Luer port 112 retards cooling of inner injection tubing body 232 and permits injecting a therapeutic substance through the opening 128 at needle tip 104.

Figure 11:
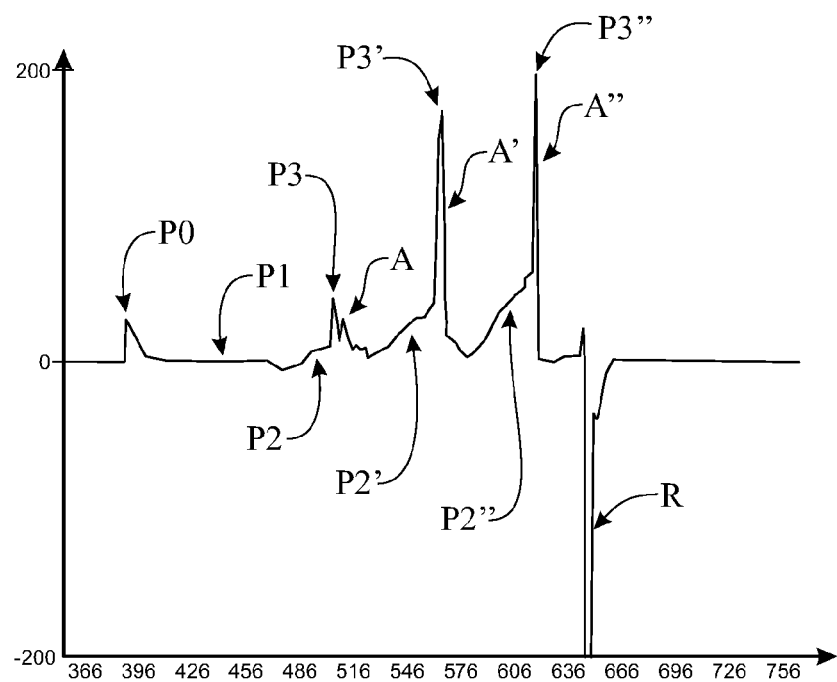
FIG. 11 presents a time vs. pressure diagrammatic profile during injection of a substance comprising Methylene Blue in a saline solution.
Figure 12:
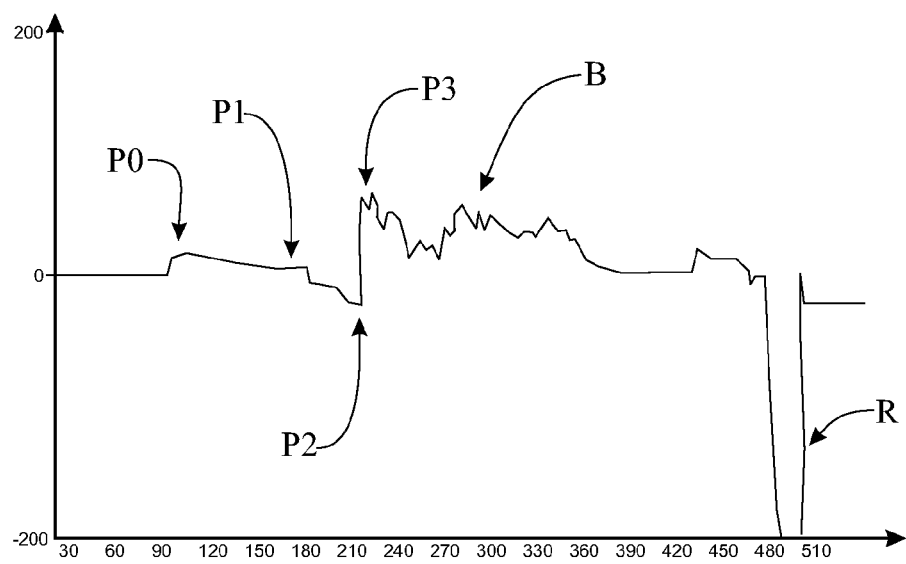
FIG. 12 presents a time vs. pressure diagrammatic profile during injection of a substance comprising Methylene Blue in an IPA solution.

When the cooling tube 232 is activated within injection lumen 218 only the non-insulated injection tip 104 will be cooled from within, as will the fluid substance and the portion of tumor 164 in contact with the needle wall 214 which will translate in fluid pressure changes as exemplified in FIGS. 11-12. The injection lumen 218 can also be used as a lumen for a smaller gauge metal needle when the goal is to deploy a delivery tip 104 out of the distal zone 226 and within the target tumor 164. The needle wall 214 and the insulation layer 216 are homogenous and fabricated from a single material such as the INSULON® SHAPED-VACUUM™ Thermal barrier (Concept Group, Inc, N.J. USA) and the likes.

Figure 4:
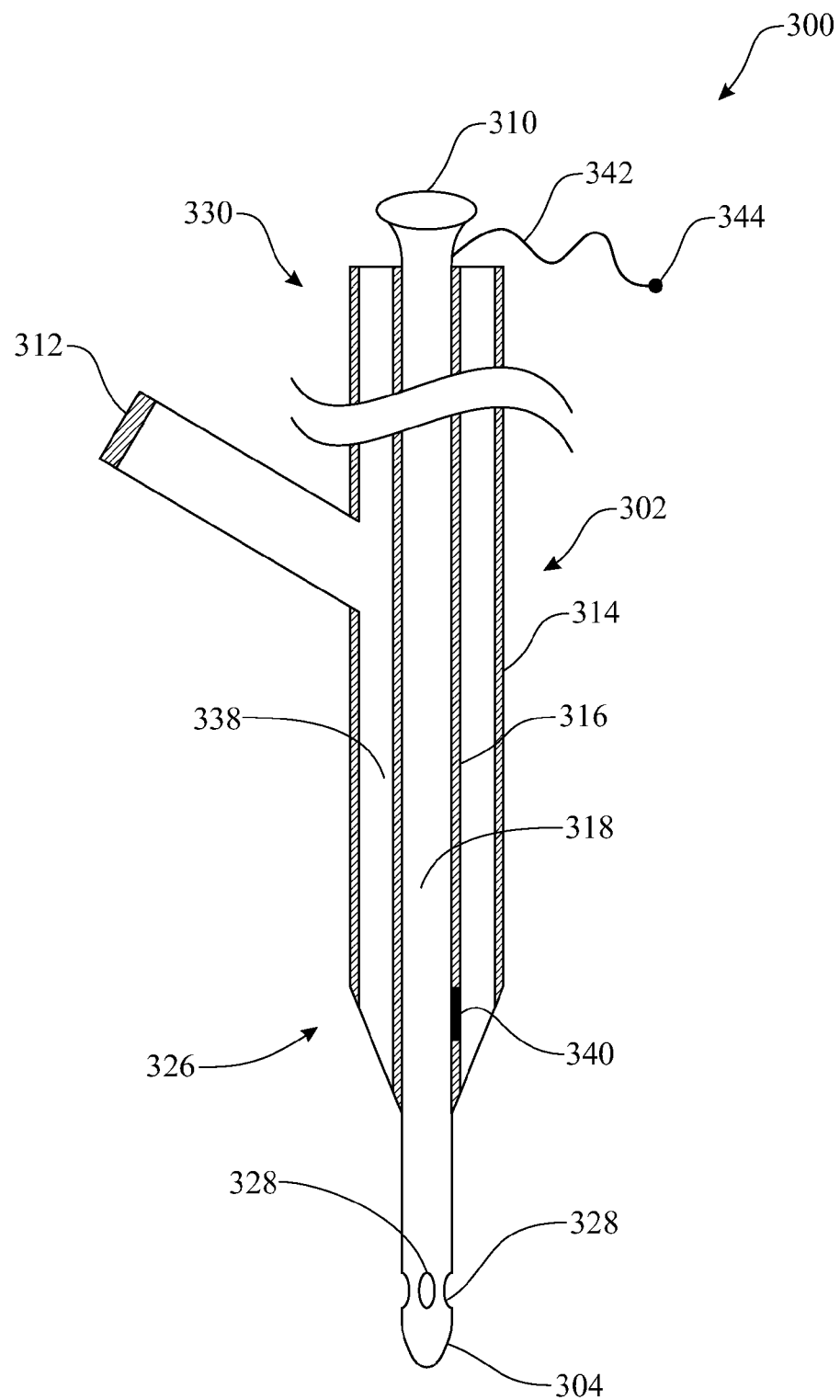
FIG. 4 presents an alternate embodiment injection needle system wherein the needle includes an air gap between an outer wall and the central lumen.

An alternate embodiment injection needle system 300 is illustrated in FIG. 4 wherein injection needle system 300 includes a needle 302 having a needle wall 314, an insulation layer 316 and an injection lumen 318 communicating with first Luer port 310 and delivery tip 304 at distal end 326 of needle 302. Needle wall 314 is provided with a second Luer port 312 at a proximal end of the needle 302. The second Luer port 312 is used to create vacuum within the gap 338 between needle wall 314 and the injection lumen 318. The vacuum is adjustable, for instances with the use of a syringe affixed to the second Luer port 312 and having a lock plunger, or the vacuum can be made permanent during the needle construction eliminating the second Luer port 312 on the side of the needle 302. The delivery tip 304 has a closed end and has side openings 328 fluidly communicative with the interior of lumen 318. The delivery tip 304 can include from 3 to 15 side openings 328 equispaced about a periphery of the delivery tip 304 and further equally spaced between 5 to 20 millimeters from the end of delivery tip 304. More preferably, there are from 3 through 12 openings 328 and most preferably 3 to 9 openings 328. The openings 328 are most preferably equally positioned 5 to 10 millimeters from the end of delivery tip 304 and can be of any desirable size from 50 to 500 micrometers in diameter provided that at least one opening 328 is free from debris, blood or obstruction such as icing during a procedure. The profile of delivery tip 304 and its geometry can vary from pointed to round. The tip and hole geometry can be close or similar to surgical needles known in the art including, but not limited to, Sprotte, Whitacre spinal needle or can be open-ended as a Quinke needle. The wall of injection lumen 318 can contain a sensor 340 to measure temperature or impedance. The sensor 340 is electrically connected to sensor cable 342 (shown in part for clarity), which is located at the proximal part 330 of needle body. Cable 61 is provided with a connector 344 at its distal end. The connector 344 is connectable to an interface cable (not shown) to a pressure monitor (not shown). Preferably the profile of the deliver tip 304 will be stepped down such that delivery tip 304 is of a smaller diameter than the distal zone of the injection needle 302. The vacuum insulation can be combined with the insulation layer 316 provided that the insulation layer 316 permits the circulation of air. The needle 302 incorporating sensor 340 can simultaneously inject fluids therethrough and conduct measurements such as pressure measurements of the fluid and surrounding tissue The injection needle system 300 as represented by the cross-section of an injection needle 302 and as shown in FIG. 3 permits injecting the substance at a single location, a technique that is desirable for small and well circumscribed lesions or tumors 164 where there is only physical space for a single cryoprobe 180 and one separate injection needle 302 or for an injection needle such as injection needle 202 provided with a cooling instrument as illustrated in FIG. 3. Preferably for small injection needles and for simplifying construction design and manufacturing costs the sensor 340 is not integrated within the needle wall.

Figure 5:
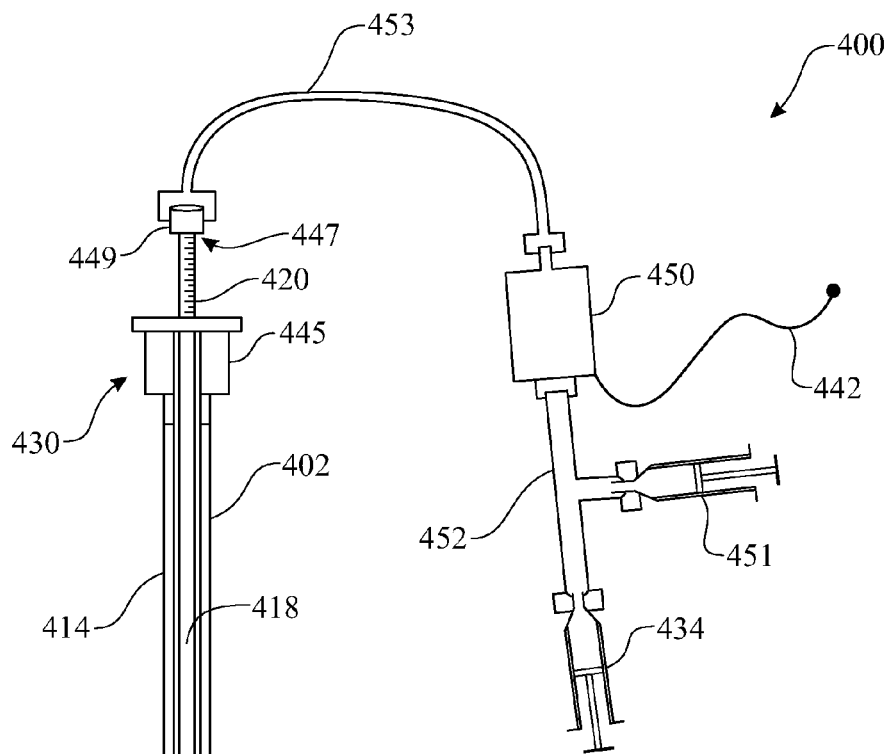
FIG. 5 presents a an isometric view of an alternate embodiment injection needle system with a deployed injection needle and having an injection source.
Figure 6:
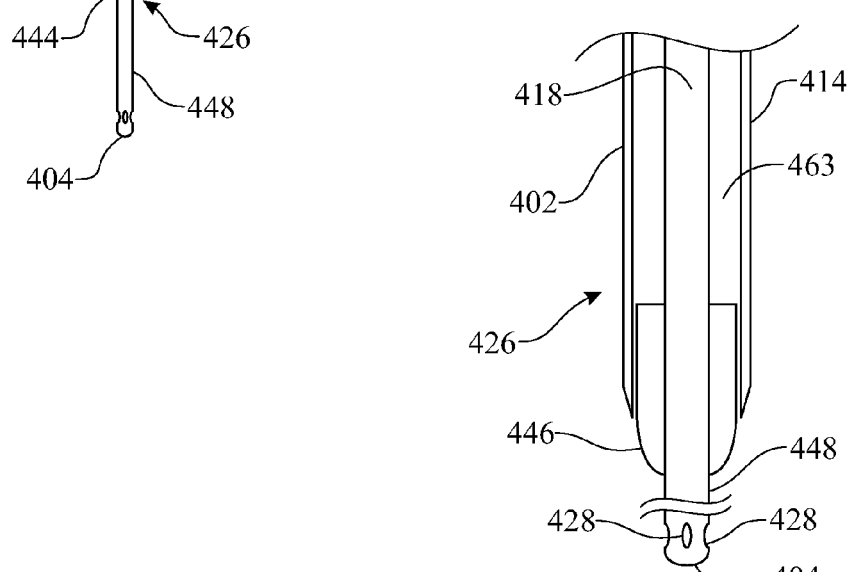
FIG. 6 presents a cross-sectional view of the injection needle tip of FIG. 5 in a retracted position.

Another alternate embodiment injection needle system 400 is illustrated in FIGS. 5 through 6 and includes an injection needle 402 having a body wall 414 and a lumen 418 extending from a needle proximal part 430 to a distal part 426. The distal part 426 of the needle 402 defines an opening 444 and receives therein an insulation centering piece 446 through which passes injection tube 448. Proximal part 430 is coupled to Tuohy Borst valve 445 that permits passage of proximal part of injection tube 448. Injection tube 448 has a distal tip 404 with side holes 428 defined therein and proximal end 447 with depth markings 420 thereon and a Luer lock hub 449. Valve 445 includes an opening to permit insertion of injection tubing 448 within lumen 418 so that distal tip 404 is deployed at a known distance from opening 444. Dehydrated air or a rare gas such argon, xenon or krypton can be provided as insulation layer 416. Luer hub 449 of injection tubing 448 can be coupled with an injection source such as a syringe or a pump. Optionally it can also be coupled with a commercially available pressure sensor 450 and monitoring system (not shown) such as an invasive blood pressure monitor unit (Datex-Ohmeda S/5 ADU Care station). Pressure sensor 450 can be a disposable blood pressure sensor and pressure line kit such as Deltran® sensor and kit (Utah Medical Products Inc.). The injection source includes a substance reservoir 451 and an injection syringe 434 coupled with a check valve 452 such as Qosina (New York, USA). The pressure sensor 450 can be in series with the check valve 452 and coupled with Luer lock hub 449 of injection tubing 448 through injection and pressure line 453 and connector. The cable 442 from the pressure sensor 450 connects to a pressure monitor (not shown). The injection tubing 448 is illustrated in its deployed position in FIG. 5. Keeping the injection tubing 448 centered within lumen 418, particularly when it is of small diameter, is the function of the cylindrical insulating centering piece 446. The insulating centering piece 446 is located along lumen 418 and can be a single segment, multiple segments, or a coil made of insulating material as is known in the art. Valve 445 can be replaced by haemostatic valve or can be connected to first Luer port 110 of connector 106 (FIG. 1) so that during a procedure a first substance of low heat conductivity can be injected within lumen 418 to decrease heat transfer to injection tubing 448 and then the therapeutic substance is injected into tubing 448. Such insulating substances include but not limited to collagen, fibrin glue foams, and the like, lipiodol (Ethiodol, Guerbet Laboratories, France), gelatin sponge particles (Gelfoam), polyvinyl alcohol foam (Ivalon), degradable starch microspheres (Spherex), microcapsules of anti-cancer drugs, etc. or mixtures of the above. The advantage of circulating a low heat conductive substance (genuine or foam formulation) within lumen 418 prior to injecting the therapeutic substance include that the formulated substance behaves as an insulating layer and as a needle tip locator, because of its imaging characteristics, upon injection into target tissue and also behaves as a drug carrier as well. For instance, a high heat capacity fluid such as a poloxamer or PLURONICS®, Surfactant Polymers (BASF) and the likes may be used for Drug Delivery. Additionally the formulation can include simple foaming with air bubbles, or with other gases such as $CO_2$.

FIG. 6 illustrates an alternate embodiment needle 402 wherein the insulation centering piece 446 is at the distal part of the injection tubing 448 and the insulative layer 416 within needle wall 414 is replaced by an air gap 463. The air contained within the gap 463 between the injection tubing 448 and the needle wall 414 is a good thermal insulator provided that the injection tubing 448 does not contact the wall 414 during a procedure. The insulation centering piece 446 functions to keep the injection tubing 448 centered during a procedure. Its length along the longitudinal axis of injection tubing 448 is such that it permits a predetermined deployment distance from opening 444.

Figure 7:
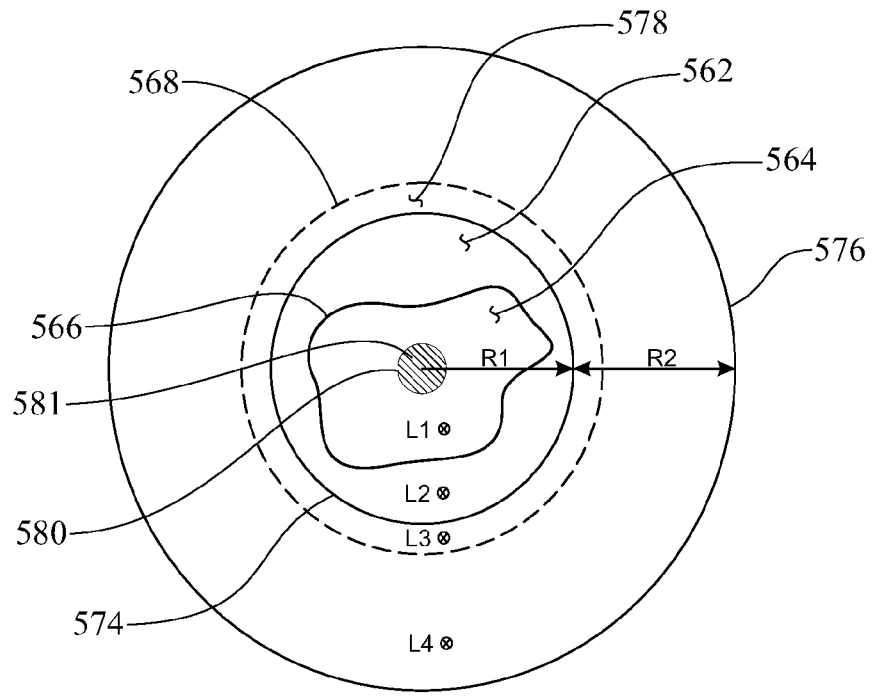
FIG. 7 presents a schematic view of a cross-section of a tumor and possible injection needle positions relative to a cryoprobe location during cooling activation.

FIG. 7 presents a schematic view of a cross section of a tumor 564 and injection needle positions (L1 through L4) relative to the location of a cryoprobe 580 during cooling activation. The cross section of the tumor 564 having an irregularly contoured tumor margin 566 is represented during a cooling sequence of a cryosurgical procedure, i.e. cryoablation with a single cryoprobe 580. Cryoprobe 580 cooling tip 581 is represented in the center of the tumor 564 and, during cryoprobe cooling, critical isotherms are shown for delineation of ice front 568 (0° C. isotherm), for cancer cell survival at margin of frozen interface 574 (−20° C. isotherm), and for peripheral margin of hypothermal zone 576 (+25° C. isotherm). R1 is the radius measured from cryoprobe 580 center to frozen interface 574 (−20° C. isotherm), which engulfs the tumor and surrounding healthy tissue (safety margin). In clinical applications the cryoablative standard protocol submits the tumor 564 and the safety margin to −20° C. and down to the cryoprobe temperature (lower than −20° C., and down to −100° C. or −140° C. depending on the cooling device and refrigerant). R2 is the radius measured from the frozen interface 574 (−20° C. isotherm) and peripheral margin of hypothermal zone 576 (+25° C. isotherm). This cooling zone includes a zone of partially frozen tissue 578, and an outer hypothermal zone 576. The zone of partially frozen tissue 578 is slushy ice, where cancer cells can survive the freezing process. Cancer cells also tend to migrate or invade healthy tissue at the tumor margin 566 within the zone of partially frozen tissue 578 and further within draining lymph nodes (not represented). The R2 surface dimension is about twice that of R1. Additionally, separate representative locations of the injection needle 102 of injection needle system 100 are represented along a Y axis at various possible locations (L1 through L4) in order to illustrate the range of possible spatial combinations: within frozen tumor 564 (L1), within frozen tissue 562 but not frozen tumor 564 at under −20° C. (L2), within partially frozen tissue 578 (L3), or within the unfrozen hypothermal zone 576 (L4). FIG. 7 illustrates that an injection of substance is desirable either within the frozen zone or the unfrozen zone depending on the intended therapeutic effect. If the intention is to drive the drug around the growing frozen zone (bounded by ice front 568 and which is impervious to water-based drug solution and many other liquid substances, hydro or lipophilic, or ampiphilic) the best injection site is in the vicinity of the frozen interface 574 (−20° C. isotherm) within the R1 region. When the goal is an exposure of peripheral and invading cancer cells to the drugs as well as to the low temperature, the best injection site is within the partially frozen tissue 578 or the hypothermal zone 576 (injection site L4). Substance injection can be performed in multiple locations simultaneously if deemed desirable.

Returning to FIG. 1 it is obvious that during a freezing sequence the non-insulated delivery tip 104 of the injection needle 102 must be positioned in an unfrozen area of the tumor or tissue even though its thermally insulated body 103 is positioned within a frozen zone 568 (frozen zone 168 in FIG. 1). In such case the delivery and flow of the liquid substance within tissue is possible. Any commercial cryoprobe 180 (cryoneedle etc.) for cryosurgery can be used in conjunction with the injection needle 102 of system 100 regardless of the cryoprobe functional characteristics. However, only closed tip cryoprobes will be used for internal or intratumoral applications. Coolant spray methods (using such refrigerant as liquid nitrogen, liquid nitrous oxide, carbon dioxide, etc.) can be used on skin lesions or surface lesions according to known indications for use for the devices. Guidance of cryoprobe 180 and injection needle 102 can be affected using direct vision or with such guiding imaging modalities as ultrasonography (US), Computerized tomography (CT), magnetic resonance imaging (MRI) or any other imaging or guiding technique know in the art. For those well practiced in the art, enhanced US imaging of the needle 102 can be obtained by providing needle tip 104 with a coating, by mechanical preparation (such as grinding), or by vibrating the needle 102 at its resonant frequency (U.S. Pat. No. 5,425,370). For MRI guidance special MRI compatible material will be used for construction of the needle 102 as known in the art. Most interventional cryosurgical procedures utilize one or multiple fine cryoneedles of 2 mm or 1.7 mm diameter (Endocare, Healthtronics, USA; Galil Medical, USA). Freezing duration for a typical clinical percutaneous procedure may vary from 5 to 15 minutes on an average, performing two freeze-thaw cycles. A larger frozen zone 168 (FIG. 1) will result from the second freeze sequence for a similar cooling duration. Frozen zone 168 (ice ball) diameters at operation reach about from 20 mm to 40 mm varying also with tissue type and blood supply. The length of ice ball 168 along the longitudinal axis of cryoprobe 180 is usually 4.5 cm. To benefit from the concurrent intratumoral freezing and injection, the positioning of the injection needle 102 relative to that of the cryoneedles 180 is based on the calculated freezing time and frozen zone dimension developing at each location of cryoprobe 180.

Figure 8:
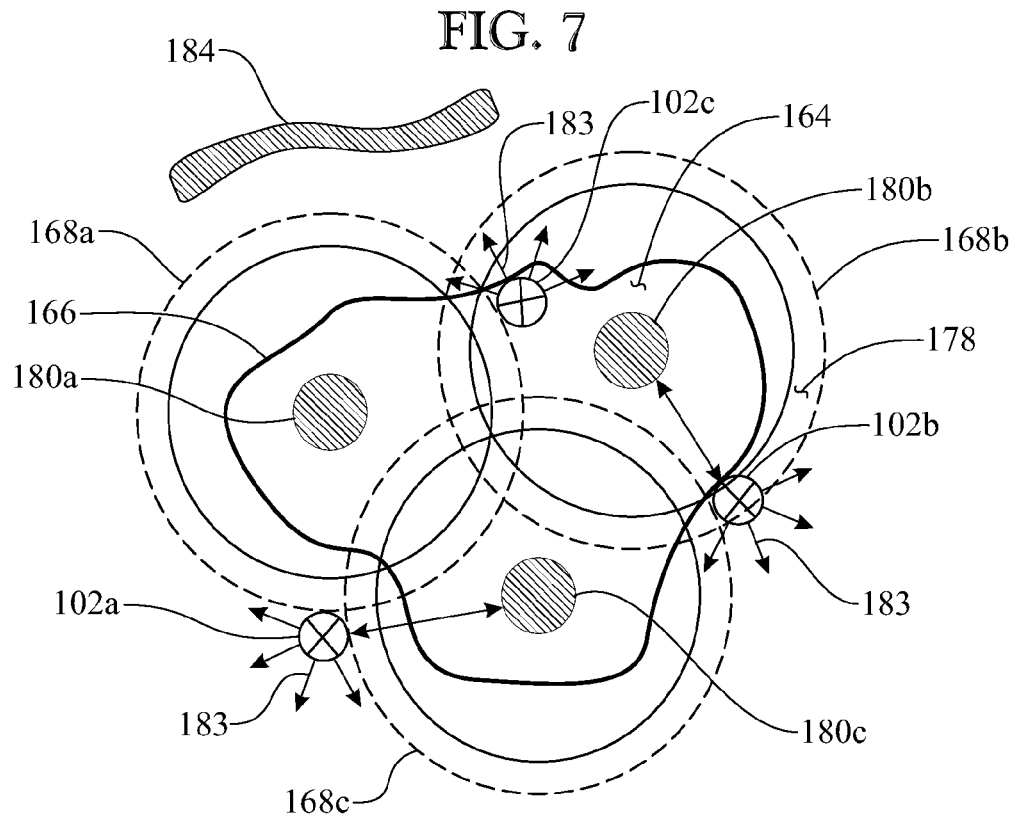
FIG. 8 presents a schematic view of a cross-section of an irregular tumor under simultaneous freezing and injection of a therapeutic substance with multiple cryoprobes and perfusion needles.

Turning now to FIG. 8, the distance/gap—double arrows-measured between the perfusion needles 102a, 102b, and 102c and the cryoprobes 180a, 180b and 180c is set by the operator and based on the timing of substance injection relative to the freeze-thaw sequence and on the selected site of injection (at 102a, 102b, and 102c) relative to the tumor and to the extent of the frozen zone. When multiple cryoprobes 180 are used for treating large or irregular tumor 164 multiple perfusion needles 102 of injection needle system 100 should also be used and interposed between adjacent cryoprobes 180 as exemplified in FIG. 8. Ideally, a perfusion needle 102 should be positioned at tumor margin 166 as for needles 102b and 102c, and within partially frozen zone 178 (position of needle 102b) or at frozen/unfrozen interface (position of needle 102a), or at overlapping frozen zone margin (position of needle 102c). During a concurrent cryosurgery and perfusion procedure such positioning of perfusion needles 102a, 102b, and 102c allows the injected substance to be convectively transported at tumor margin 166, as represented by substance propagation arrows 183 during a freeze sequence and for the substance to be trapped within frozen and melt zone during a thaw sequence. At the position of needle 102c the liquid substance is transported in the vicinity of risky, sensitive or heat sink structure 184 such as a large blood vessel that should not or cannot be properly cryotreated. An optimal separation between a perfusion needle 102 and one or two adjacent cryoprobes 180 is within a range of from 1 cm to 3 cm, or from 0.5 cm to 2 cm or less than 0.5 cm or greater than 3 cm provided that the perfusion needle 102 is within the R1 (−20° C. isotherm) zone or the partially frozen tissue zone 178 when one desires the injected substance to flow away from the frozen zone 168 and within the R2 hypothermal zone (out to the +25° C. isotherm) when the substance deposition is targeted for outside the frozen zone 168. During the thaw sequence, when ice balls 168a, 168b, and 168c melt, substance delivery can be performed within the R1 (−20° C. isotherm) zone and R2 hypothermal zone (out to the +25° C. isotherm) for facilitated substance permeation of the tumor 164 and tumor cells and for possible prolonged substance retention time at the sites of substance delivery. Cryoprobe 180 can also be within perfusion needle 202 as exemplified in FIG. 3. In that case the substance will flow within passageway 236 of FIG. 3 and its delivery will be at the injection tip of perfusion needle of FIG. 3 similar to the injection tip 104 of perfusion needle 102; the frozen zone will develop proximal to injection openings 228 so that the fluid substance will be transported away from frozen zone 168 during the activation of cryoprobe 180 and the substance delivery procedure.

Figure 9:
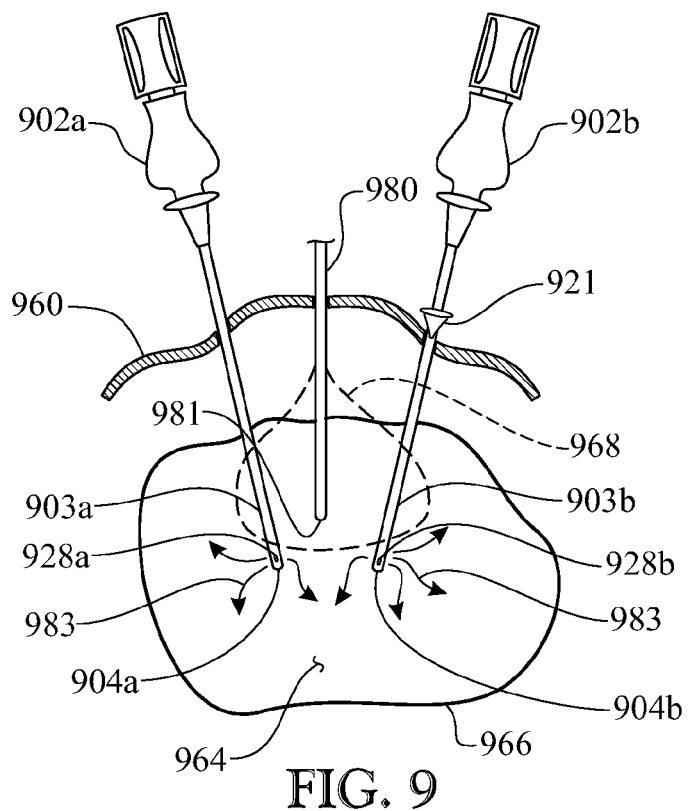
FIG. 9 presents a schematic view of a frontal section of a tumor during intralesional cryotherapy and the simultaneous injection of a liquid therapeutic substance.
Figure 10:
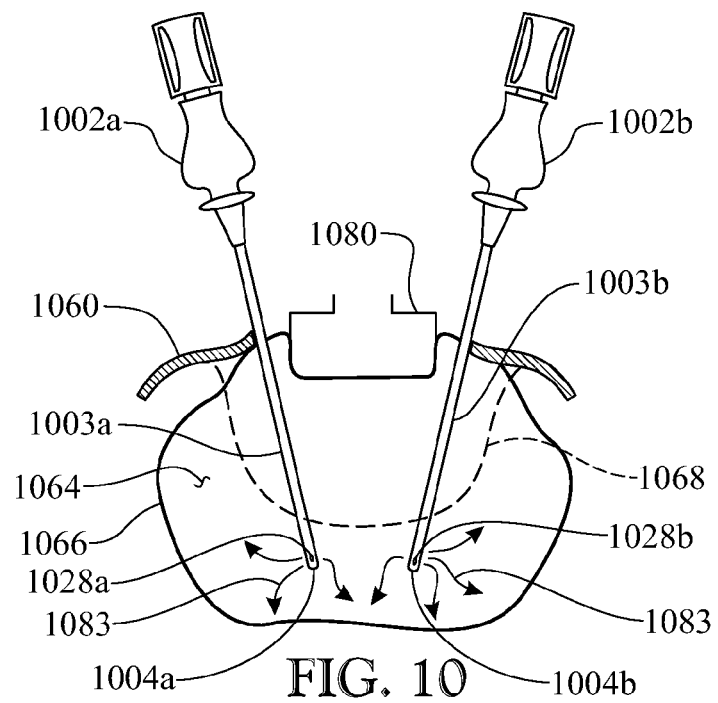
FIG. 10 presents a schematic view of a frontal section of a tumor during surface cryotherapy and simultaneous intralesional injection of a therapeutic substance.

FIGS. 9 through 10 illustrate a schematic view of a frontal section of a tumor during intralesional cryotherapy. FIG. 9 illustrates the procedure as related to treatment of a deep-seated tumor, and FIG. 10 illustrates the procedure as related to surface cryotherapy of a superficial tumor. Each procedure incorporates simultaneous intralesional injection of a liquid substance at the tumor margin.

As illustrated in FIG. 9 the percutaneous approach uses a cryoprobe 980 and two perfusion needles 902a and 902b according to an embodiment of the invention. Cryoprobe 980 and the two perfusion needles 902a and 902b penetrate the patient's skin 960 in a manner such that the perfusion needles 902a and 902b are placed in the vicinity of the cryoprobe 980 so that during freezing their shaft 903a, 903b but not their tips 904a, 904b are embedded into the frozen zone 968 of tumor 964. A depth indicator 921 helps with positioning the tip 904b of the perfusion needle 902b at the desirable depth relative to the tip 981 of the cryoprobe 980 and expected frozen zone 968. Delivery of liquid substance during freezing is possible as shown with substance propagation arrows 983 exiting the side openings 928a, 928b of needle tips 904a, 904b respectively. It should be noted that the water-based liquid substance does not permeate the frozen zone margin 968 due to its transient imperviousness. Additionally, since most tumor tissues are rich in water and since there is a volume expansion resulting from the phase change of water into ice, a pushing force for the liquids located at the interface of the frozen/unfrozen tissue 968 develops. The liquid substance delivered at this interface is directionally flowing away from the ice as represented with substance propagation arrows 983. Such directional flow is of utmost interest to drive the liquid therapeutic substance at margin 966 of tumor 964 and in the zone of cell escape and invasion, particularly for large or irregular lesions where cryoablation has shown limitations and recurrences. The fact that such fluid substance delivery is possible only during the freezing sequence of a cryoablation procedure makes the needle system uniquely adapted to the use.

As illustrated FIG. 10 a flat cryoprobe 1080 is superficially embedded at skin lesion 1064 or on a lesion of an internal organ that is accessible through open surgery or per-endoscopic approaches. The substance perfusion needles 1002a and 1002b have been inserted through the patient's skin 1060 in the immediate vicinity of the lesion 1064 and positioned relative to the location of the cryoprobe 1080 and within the tumor margin 1066 prior to the freezing sequence. During the freezing sequence the needle shafts 1003a and 1003b are embedded in the frozen zone 1068 created by the cryoprobe 1080 during the freezing sequence. The liquid substance is then delivered through openings 1028a, 1028b at needle tips 1004a, 1004b respectively and results in the substance flowing about and away from the frozen zone 1068 at tumor margin 1066 along the direction of substance propagation arrows 1083. A perfusion needle 1002a, 1002b can be implanted within tissue in any direction relative to the longitudinal axis of the cryoprobe or the advancing isotherms. A needle guide (not shown) can be used on the surface of the skin 1060 to help orient the needle track towards targeted area of lesion 1064 or other tumor being treated. Computer-aided guidance permits tracking and guiding the perfusion needle with precision within the target tumor during image-guided intervention. A well known tandem technique for cryoablation uses a first needle that is positioned within target lesion under US, CT or MR imaging and serves as a guide for the cryoneedles to be positioned in a parallel direction at various distances from the guide needle and within the tumor.

Graphs showing the time-pressure (P) profiles during bolus injection with an injection needle 202 (FIG. 3) of two substances having different properties are illustrated in FIGS. 11 through 12. An injection source as illustrated in FIG. 5 using a pressure line and a pressure sensing system is described. The substance utilized for treatment in the graph representations is Methylene Blue diluted in isotonic saline (0.9% NaCl) solution (lowest freezing or eutectic point −22.12° C.), FIG. 11, or diluted in Isopropyl alcohol (IPA) 99% solution (isopropanol base water solution freezing point −73° C., FIG. 12). Pressure (P) changes are observed when an open end 14 gauge perfusion needle equipped with an inner cooling source is immersed, activated, and removed from an Agar 0.6% phantom. There is an immersion phase when P increases briefly, immersion peak Po, then P drops and stabilizes at a base line pressure P1, followed by a pre-injection cooling period of 30 seconds upon cryosource activation at cryoneedle lowest or selected temperature, which increases the fluid substance pressure P2, and simultaneously freezes substance and tissue (a change of phase that increases the substance volume). No flow of the therapeutic substance at injection tip 204 of lumen 218 (FIG. 3) occurs, and fluid can be pressurized (pre-injection fluid pressurization), in this case manually (by pushing the piston of the syringe containing the substance) at desirable pressure P3. Cooling is stopped and active rewarming of the cryoneedle melts the substance during Phase A, which translates in a rapidly decreasing fluid pressure. The substance flows within the patient's tissue and is prevented from flowing back through the needle track by frozen ice ball 168 (FIG. 1) that occludes the needle trace 170. Upon the pressure reaching a value close to base line P1, if the entire dose of the substance has not been injected (depending on operator preferences, desirable flow rate, substance characteristics, etc.), another cooling sequence P2' can be performed to a pressure P3' prior to another re-warming, fluid release sequence, A' for perfusion needle such that the Methylene Blue in saline can melt and flow. Another cooling, fluid pressurization, fluid release sequence is possible such as P2"-P3"-A" etc. Upon delivery of the entire dose of substance, the perfusion needle can be removed and continued pressure readings are helpful in indicating when the residual tissue pressure has reached a sufficiently low level, i.e. to base line P1 or below base line. Once the residual tissue pressure has sufficiently decreased, a fast needle removal and simultaneous suction translating into a negative pressure (R) facilitate a better collapse of the needle track and prevention of post injection flow back. The ratio P2/P1 is an indicator of the fluid valve status either open or closed (open when substance is in fluid form and closed when substance is frozen) of the perfusion needle during the pre-injection cooling period, and this indicative ratio may vary from 2 to 6, or from 1.5 to 4, or from 1.2 to 3.

FIG. 12 illustrates a graph similar to that of FIG. 11 wherein the substance Methylene Blue is diluted in IPA 99% with pressure changes happening in a similar order as the pressure sequences of FIG. 11. However, since the IPA 99% freezing point (−73° C.), thermal capacity, thermal conductivity, and thermal expansion, is quite different compared to the saline solution utilized above, the pressure P2 during the first pre-injection cooling decreases and the P2/P1 ratio may range from 0.2 to 0.5, or 0.3 to 0.4, or 0.25 to 0.55. However, this ratio may vary depending on a specific perfusion needle design and the therapeutic substance being administered. FIG. 11 further illustrates that IPA 99% Methylene Blue can be injected at low pressure P3 during continuous cooling (phase B) and no significant active rewarming of the cryoprobe tip is necessary to facilitate its free flow. Additionally, a mixture of the therapeutic substance may have a pattern of pressure changes that reflects the melting point of the mixture. For a solution of a substance with various solvents the freezing/melting point of the solution, as well as other properties, will determine the time when during cooling it will freeze and self solidify, or melt and flow. For instance, for a 70% IPA/water mixture the freezing point is −29° C. The aspect of the pressure-time profiles will vary accordingly. When the cryoneedle or the perfusion lumen are equipped with a thermocouple, the time-temperature profiles (not shown) can be recorded and used as complimentary parameters to time-pressure profiles.

Figure 13A:
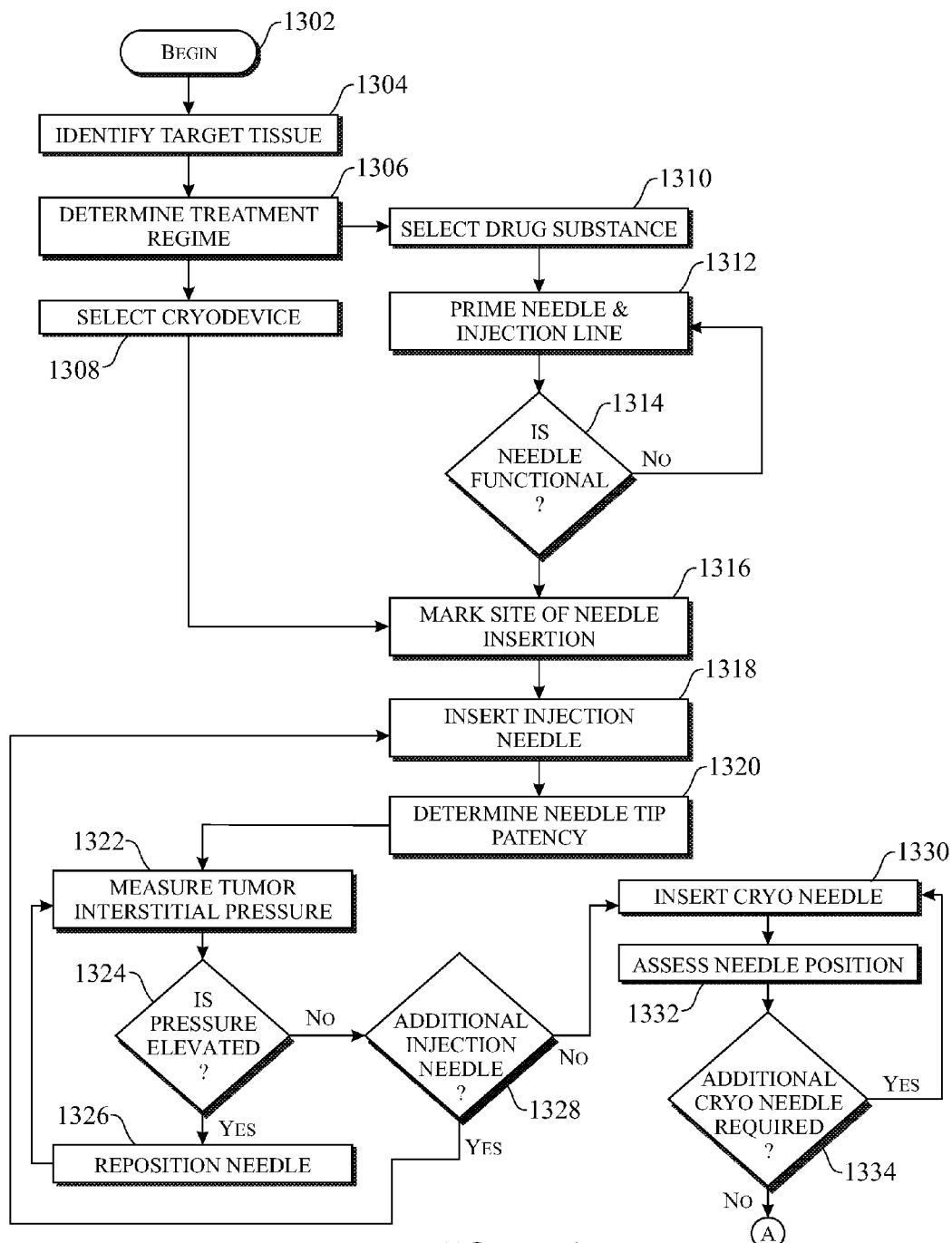
FIGS. 13A and 13B collectively present a block diagram flow chart of a concurrent cryotherapy and injection procedure.
Figure 13B:
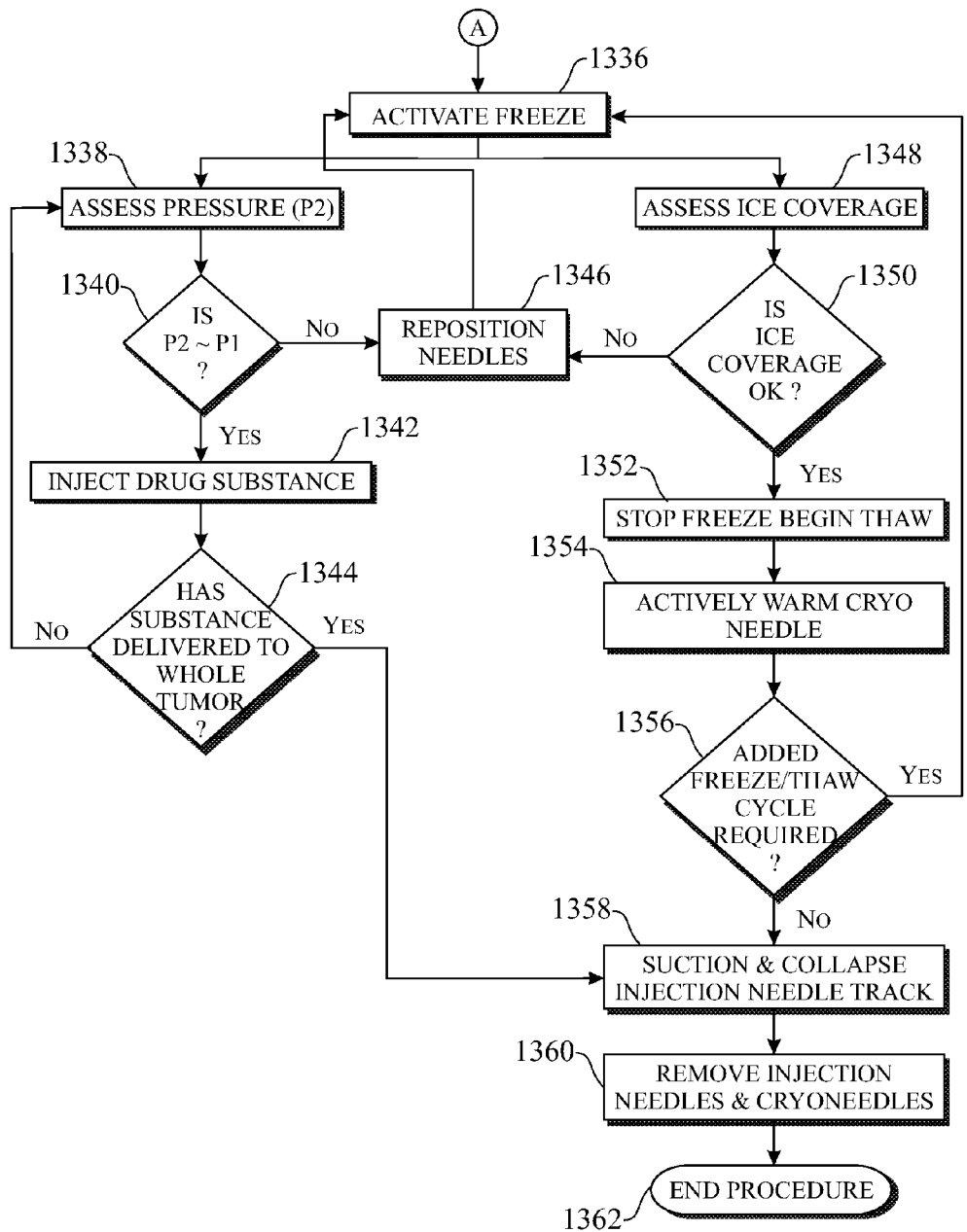

FIG. 13 presents a block diagram of a process for concurrent single site cryoablation and bolus injection of a cytotoxic substance procedure for an image-guided percutaneous approach of a deep-seated tumor utilizing an injection needle system such as system 100 as illustrated in FIG. 1. The injection needle 102 is separate from cooling sources, such as the cryoprobes, and has closed tip profile 104 with side openings 128. The process begins at block 1302, and the tissue to be targeted for treatment, such as a tumor 164 is identified in block 1304. In block 1306 a treatment regime for the tumor 164 is determined for utilizing an injection needle system 100 and a cryogenic device such as cryoprobe 180 is selected in block 1308. Concurrently, a treatment substance is selected and the maximum dose of the substance to be injected is calculated in block 1310. The calculated dosage is based on the calculated tumor volume according to known formulas.

Once the treatment substance, dosage and the cryogenic device for use have been selected, the process continues in an operating room or such facility supportive of a percutaneous interstitial cryosurgery and therapeutic substance injection procedure with interstitial pressure monitoring. In block 1312, the injection needle 102 and injection line is primed with liquid substance and in block 1314 the needle 102 and line are assessed to insure the absence of bubbles and the functionality of the needle 102. If deficiencies in the needle 102 and the line are discovered or bubbles are found in the line, the process returns to block 1312 to again prime the needle and line. In block 1316, the site of the insertion of the needle 102 is marked on the surface of the patient's skin 160 in further preparation for the treatment. The first injection needle 102 is inserted through the patient's skin 160 in block 1318 and the tip 104 is guided to the target tissue using selected optimal track with imaging modality. In block 1320 the proper positioning and functionality of the needle 102 within tumor 164 and preferably at or near the most remote tumor margin 166 is determined. Injection of a small amount of contrast agent is used where needed, such as when tip 104 of needle 102 isn't seen well.

Upon insertion of the injection needle 102 within the target tissue and verification of the patency of the needle tip 104, the interstitial pressure, or initial base line pressure P1 is measured in block 1322. The pressure is indicative of the relative interstitial pressure of the tumor at the tip 104 of the properly primed needle 102. If in block 1324, the medical professional determines there is an elevated pressure reading on a monitor prior to initiation of cryoablation, the elevated pressure could indicate a tumor zone of low compliance (fibrous, hyperdense) that may not be optimal for substance injection. In such case the medical professional performing the procedure may then decide, in block 1326 to reposition the needle 102 at a better site showing a lower pressure. Once the needle 102 has been repositioned the process returns to block 1322 to again measure the tumor interstitial pressure. The cycle represented by blocks 1322-1326 repeats until the medical professional determines that the measured pressure is not elevated and thus satisfactory whereupon the process proceeds to block 1328 for determination whether additional injection needles 102 are to be placed in the patient's tissue. If additional needles are necessary, the process returns to block 1318 for insertion and verification of the placement of the next and subsequent needles.

When all desired injection needles 102 have been inserted, properly placed, and verified the process proceeds to block 1330 to insert cryoprobe 180 in tandem at a selected distance and in similar direction into tumor 164. The cryoprobe tip 181 is positioned proximal to injection needle tip 104 in block 1332 and the position of the cryoneedle tip 181 is verified. In block 1334, the medical professional determines if an additional cryoneedle 180 is required. If so, the process returns to block 1330 for insertion of an additional cryoneedle 180 the cycle repeats until all desired cryoneedles are inserted and verified as to placement of the needle tips 181.

Once all of the injection needles 102 and cryoneedles 180 have been placed, the process proceeds to block 1336. In block 1336 the cooling sequence of the first freeze/thaw cycle is commenced and the progress of the cooling as represented by a growing frozen zone 168 is imaged on the monitor screen of an imaging modality (either ultrasound, computerized tomography or magnetic resonance imaging). At this point, the medical professional must concurrently monitor and assess both the pressure change (pressure P2, FIGS. 11 through 12) in block 1338 and the ice coverage of the progress of the freezing induced in the tumor 164 by cryoprobes 180 in block 1348.

Starting with block 1338, the pressure P2 is monitored and assessed. If in block 1340, pressure P2 is approximately equal to the base line pressure P1, the medical professional in block 1342, starts injecting the drug substance from 0 through 30 seconds to 60 seconds and up to from two to ten minutes after initiation of cooling. The professional injects a dose of substance during cooling and tissue freezing as imaged on the monitor(s) and according to known efficacy criteria known as "ice coverage". For instance an initial dose of one-third (⅓) of the total calculated dose for the volume of tumor 164 may be injected and visualized during permeation through the tumor interstitial compartment, (ECM) on the screen of a CT scan. If, in block 1344, it is estimated that the substance distribution is not homogeneous or complete, as imaged on a US, CT or MR image, the process returns to block 1338 and a second bolus injection is performed and so on until proper freezing (ice ball) and filling of the tumor with substance known clinically as "contrast-drug tracer coverage" is observed at or in near real time imaging when the substance is mixed with a tracer (a marker that can be a radiocontrast molecule, an echogenic molecule or a contrast agent for magnetic resonance imaging). Since most clinical percutaneous cryoablation applications using argon-based minimally invasive cryoneedles have freezing duration sequences of between 10 and 15 minutes or more, there is plenty of time for sequential substance injections. If, for some reason the flow of liquid substance is interrupted before proper dosage of the tumor 164 with the substance has been achieved (blockage at the lumen or the delivery tip 104 from unwanted tip 104 immersion within the frozen zone 168 that translates in large pressure change P2 from the base line pressure P1), the rest of the dose is injected during the $1^{st}$ thaw period or at a repeated cryocycle. Usually a cryoablative procedure requires at least two successive freeze/thaw cycles. If it is estimated that the frozen zone and the substance filling are achieved before administration of full calculated dose of substance there is no need to prolong freezing or injection. It has been observed in clinical practice that less than 70%, or 50% or 30% of the calculated dose can actually permeate a cryotreated tumor. Preferably, when the tumor interstitial pressure and injection pressure are to be used, the base line pressure P1 is measured with the injection needle 102 properly inserted prior to cryoablation, during cryoablation, during substance injection, and after cryoablation and completion of injection. Pressure readings observed during the procedure are used to accommodate the injection site and to adjust the time and rate of injection of the substance. If, however, pressure P2 is not approximately equal to the base line pressure P1 in block 1340, the needle 102 is repositioned in block 1346 and the process returns to block 1336 to again activate the freeze process.

If the injection needle 102 is properly positioned, the medical professional looks for possible pressure changes occurring from substance cooling when the ice margin 168 approaches the non-insulated tip 104 of the injection needle 102 containing the substance in determining whether the ice coverage is acceptable in block 1348. Any minimal pressure change is an indication that substance is experiencing the start of a change of state due to cooling and that it's time to start injecting the calculated dose of the substance. By doing so the medical professional knows that the frozen zone 168 will assist in the distribution of the substance away from the frozen zone and in the direction of the more peripheral tumor margin 166. Cooling need not be discontinued during injection provided that the rate of substance injection is maintained sufficiently to prevent it's freezing. Additionally, the injection pressure is adjusted, such as by pushing on the plunger of the syringe containing substance, to be slightly more elevated than the base line pressure P1 so that the fluid substance doesn't fracture the tumor paths of low resistance. The substance thus tends to be better distributed over the tumor volume. Another advantage of continuously measuring the pressure at the site of the needle tip 104 is to indicate continuous patency of the injection lumen and flowability of the substance at any time during the freezing procedure, provided that the pressure readings stay at or near base-line pressure P1.

If the ice coverage is deemed to be inadequate in block 1350, the medical professional is directed to block 1346 where the needles can be repositioned and then redirected to block 1336 to again restart the freeze cycle. Howver, if the ice coverage is deemed to be adequate, the process proceeds to block 1352 where the freeze process can be stopped and the thaw process begun. In block 1354 the cryoneedles 180 are actively warmed to facilitate thawing.

After the procedure has been completed the pressure readings allow evaluating the residual pressure and immediate tissue response to the combined therapy. They also allow optimization of the removal time for the injection needles 102. Injection needles 102 should preferably be removed from tumor 164 when the interstitial pressure has returned to or under the base line level. It is believed that when pressure is lower than base line readings the substance has been widely distributed and the tumor is probably undergoing vascular deprivation. When the desired freeze and drug delivery has been achieved, such as at full freeze dose and full delivery of substance dose, the cryoneedles 180 are actively re-warmed in block 1354 and removed from the target tissue, and then the injection needles 102 are left in situ for 10 minutes or until the interstitial pressure (if measured) returns to base line level P1. If an additional freeze/thaw cycle is deemed necessary in block 1356, the process is returned to block 1336 to begin a new freeze and substance injection as necessary. If no further freeze/thaw cycles are required and if, in block 1344 sufficient substance has been delivered to the tumor 164, the process continues to block 1358 where the needles 102 are then slowly removed and the needle track can be collapsed by providing suction to the needles 102 during removal. Alternatively the needle track 170 can be filled with a biocompatible and bioresorbable plug such as fibrin glue, collagen or any suitable agent known in the art. Completion of injection needle 102 and cryoneedle 180 removal is accomplished in block 1360 and the procedure ends in block 1362.

If an injection needle of FIG. 3 is simultaneously used for cooling the tumor 164 and delivering substance to the target tissue, the pressure variations observed are represented in diagrams FIGS. 11 through 12. Now referring to FIG. 11, cooling at the tip of the needle will cool down the substance first and then the surrounding tumor. A steep pressure change P2 varying with substance characteristics compared to base line pressure P1 will be observed from the substance freezing and pre-injection pressurization P3. The substance will be injectable only when a fast re-warming of the cooling tube 232 within a few seconds is activated in A, A' or A" as illustrated in FIG. 12. Such needle patency will be immediately apparent at an abrupt drop of pressure A, A' and A" for a saline solution. At this time pushing on the plunger of the syringe containing the substance will result in an increased pressure that can be adjusted to be a slightly more elevated than baseline pressure P1 and maintained during delivery of the substance dose to the tumor 164. The substance utilized in FIG. 12 has a low freezing point since it contains isopropyl ethanol. Therefore, the pressure changes observed are different from those observed with the saline solution utilized in the graph of FIG. 11, but the variations are still indicative of substance injectability. The P2 cooling pressure will show a negative variation compared to P1 and the pre-injection pressure P3 can be adjusted for substance delivery during phase B. R is the negative pressure exerted on the fluid during aspiration of fluid within the syringe when removing the needle from the tumor 164.

When multiple injection needles and cryoprobes are used, a similar procedure is followed which consists in first positioning the injection needles and secondly positioning the cryoprobes according to optimal tracks for the tumor approach. Usually the needle tips are more distal than the cryoprobe tips in order to avoid engulfing the injection needles' delivery tips into the frozen zone. The injection needles and cryoprobe shafts are spaced to allow coverage and overlapping of the frozen zones, more centrally located in the core of tumor, along with the substance injection zones, more peripheral to the tumors.

When the purpose is to inject during the thaw period, a similar procedure for positioning injection needles relative to the location of the cryoprobes is followed. The injection of the substance is preferably made during the thawing period of the first freeze/thaw cycle or at any subsequent thaw period of additional freeze/thaw cycles.

When the ablation purpose is palliative, such as when the intent is to accomplish such objectives as, including but not limited to, downsize a large tumor, kill as many metastatic tumors as possible, relieve pain, or to address blood loss from a growing tumor, the largest frozen zones possible must be formed and the distribution of the substance must be achieved at the margin of the confluent frozen zones. In such case the substance delivery may be initiated at the end of the freeze period. Additional freeze and delivery sequences may also be used when the purpose is to progressively permeate the tumor with a drug substance. Such procedure is typically called "freeze and drug delivery waving" and calls for dividing the freeze duration and substance dose calculated to cover a tumor target in multiple short freeze/thaw and drug delivery periods. For instance at a first deep freeze period that freezes a third of the targeted tumor, a third of the substance dose is injected while the frozen front is maintained at a shallow freeze, a repeated cool/thaw cycling process that is sufficient to maintain the ice zone but unable to grow it larger. A second deep freeze period will freeze about two-thirds (⅔) of the target and an additional third of the substance dose is injected during stabilization of the frozen front (ice margin 0° C.). At a third deep freeze period most if not all the target is within the ice margin and the last third of the substance dose is injected. Such procedure overlaps each frozen zone and substance permeated zones in growing areas and combines the "push" of the substance during cooling and the "pull" trapping/permeation of the substance during ice margin stabilization or during thawing. A major advantage of injecting during freeze is the prevention of substance backflow within needle track. Another advantage is the immediate permeation of tumor cells and or vasculature with the therapeutic substance due to the physico-chemical effects of freezing. Additionally, the increased matrix porosity at each freezing sequence helps with a wider and more homogeneous distributing of the substance. When the intended target freeze (ice coverage) and calculated drug dose delivery has been achieved, such as at full freeze dose and full delivery of substance dose, the cryoneedles are actively re-warmed and removed from the target. The injection needles are then left in situ for 10 minutes or until interstitial pressure (if measured) returns to base line level P1 and the needles are then removed slowly and the needle track is usually filled with a biocompatible and bioresorbable plug such as fibrin glue, collagen or any suitable agent known in the art.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What I claim is:

1. A perfusion needle system for the direct simultaneous injection and flow of a therapeutic substance fluid within a target tissue during cryothermal ablation of the target tissue, said perfusion needle system comprising:
    at least one cryogenic probe for insertion in a patient's bodily tissue, said cryogenic probe having a cooling tip for selective cooling and thawing of the tissue;
    an injection syringe containing a fluid therapeutic substance;
    a pressure line fluidly connected to said injection syringe, said pressure line including a pressure sensor configured to interface with a pressure sensing system for determining pressure of said fluid therapeutic substance in said pressure line; and
    at least one insulated injection needle fluidly communicative with said pressure line, said insulated injection needle comprising:
    a port at a proximal end of said insulated injection needle for connecting to said injection syringe;
    a tubular insulated needle body having a wall forming said tubular body;
        an insulative layer affixed to an interior of said wall, said insulative layer defining a central lumen extending through said body;
        an injection tip affixed to distal end of said insulated injection needle, said injection tip being devoid of said insulative layer and defining at least one opening of said injection tip and fluidly communicative with said lumen.

2. A perfusion needle system according to claim 1 wherein said injection needle tip has a smaller diameter than said insulated needle body.

3. A perfusion needle system according to claim 1 wherein said injection tip defines a single opening at an end of said injection tip.

4. A perfusion needle system according to claim 1 wherein said injection tip defines a plurality of side openings substantially equally spaced about a periphery of said injection needle tip and longitudinally equidistant from an end of said injection tip.

5. A perfusion needle system according to claim 1 wherein said fluid therapeutic substance is selected from a group consisting of a chemotherapeutic, a cytotoxic, a cytostatic, a chemicals solvents, a biologic drug, a vaccines, a gene, a drug vector, a radioisotope, a radioseed, a radiosensitizer, a protein, a cryoprotective solution, and a cryosensitizing solution, or combination thereof.

6. A perfusion needle system according to claim 1 wherein said pressure sensor is positioned in said injection needle proximate to said injection tip, said pressure sensor being electrically communicative with a pressure monitor for displaying a sensed pressure in the patient tissue at said injection tip.

7. A perfusion needle system according to claim 1 wherein said pressure sensor is positioned in said pressure line proximate to said port at proximal end of said injection needle, said pressure sensor being electrically communicative with a pressure monitor for displaying a sensed pressure in the patient tissue at said injection tip.

8. A perfusion needle system for the direct simultaneous injection and flow of a therapeutic substance fluid within a target tissue during cryothermal ablation of the target tissue, said perfusion needle system comprising:
    at least one cryogenic probe for insertion in a patient's bodily tissue, said cryogenic probe having a cooling tip for selective cooling and thawing of the tissue;
    an injection syringe containing a fluid therapeutic substance;
    a pressure line fluidly connected to said injection syringe, said pressure line including a pressure sensor configured to interface with a pressure sensing system for determining pressure of said fluid therapeutic substance in said pressure line; and
    at least one insulated injection needle fluidly communicative with said pressure line, said insulated injection needle comprising:
    a port at a proximal end of said insulated injection needle for connecting to said injection syringe;
    a tubular insulated needle body having a wall forming said tubular body; an insulative layer affixed to an interior of said wall, said insulative layer defining a central lumen extending through said body; said tubular needle wall and said insulative layer are homogeneous and fabricated from a single material;
    a central tube extending within said lumen, said central tube having a diameter smaller than said lumen and in combination with said lumen defining a gap between said central tube and said lumen, said gap fluidly communicative with said syringe; wherein said central tube is a cryogenic cooling tube, said cryogenic cooling tube selectively operable to cool tissue and rewarm tissue quickly;
    an injection tip affixed to distal end of said insulated injection needle, said injection tip being devoid of said insulative layer and defining at least one opening of said injection tip and fluidly communicative with said lumen.

9. A perfusion needle system according to claim 8 wherein said tubular needle wall and said insulative layer are homogeneous and fabricated from a single material.

10. A perfusion needle according to claim 8 wherein said injection needle tip has a smaller diameter than said needle body.

11. A perfusion needle according to claim 8 wherein said injection needle tip defines a plurality of side openings substantially equally spaced about a periphery of said injection needle tip and longitudinally equidistant from an end of said injection tip.

12. A perfusion needle system according to claim 8 wherein said pressure sensor proximate to said injection tip, said pressure sensor being electrically communicative with a pressure monitor for displaying a sensed pressure in the patient tissue at said injection tip.

13. A perfusion needle according to claim 8 wherein said tubular needle wall and said insulative layer are fabricated from different materials.

14. A method for controllably injecting a therapeutic substance to a tissue simultaneously subjected to a cryoablation treatment, said method including the steps of:

using a perfusion needle system of the type comprising at least one cryogenic probe having a cooling tip, an injection syringe containing a fluid therapeutic substance connected to a pressure line including a pressure sensor and at least one injection needle fluidly communicative with the pressure line wherein the injection needle further includes a port at a proximal end for connecting to the injection syringe, a tubular needle body having a wall forming the tubular body, an insulative layer affixed to an interior of the tubular wall and defining a central lumen extending through the body, and an injection tip affixed to a distal end of the injection needle, the tip being devoid of the insulative layer and defining at least one opening extending through a side of the injection tip and fluidly communicative with the lumen;

positioning the tip of the injection needle within a target tissue to be treated in a patient;

positioning the cryogenic probe proximate to the target tissue to be treated such that the injection needle will be within a zone of the tissue to be frozen by the cryogenic probe;

measuring a base line fluid pressure;

activating the cryogenic probe to produce a zone of frozen tissue extending about a body of the injection needle and excluding the tissue about the injection needle tip;

delivering the fluid therapeutic substance through the injection needle tip when the zone of frozen tissue approaches the injection needle tip;

allowing a desired dose of the fluid therapeutic substance to distribute through the target tissue at a pressure above the baseline pressure and propagated away from the zone of frozen tissue;

assessing the pattern and volume of substance distribution within the target tissue;

removing the injection needle from the target tissue when the pressure reading is at or below the baseline pressure; and removing the cryogenic probe when the target tissue frozen zone has thawed.

15. The method according to claim 14 wherein the targeted tissue is a tumor and the tissue frozen zone encompasses the entire tumor.

16. The method according to claim 15 wherein the fluid therapeutic substance is at least partially distributed in tissue outside the margin of the tumor.

17. The method according to claim 14 wherein a plurality of injection needles and a plurality of cryoprobes are inserted in the target tissue, each cryoprobe producing a frozen zone and further wherein the frozen zones of adjacent cryoprobes overlap one with the other and each injection needle delivers a dose of fluid therapeutic substance overlapping with a dose of fluid therapeutic substance of an adjacent injection needle.

* * * * *